(12) United States Patent
Näsholm et al.

(10) Patent No.: US 9,481,610 B2
(45) Date of Patent: Nov. 1, 2016

(54) USE OF A FERTILIZER CONTAINING L-AMINO ACID FOR IMPROVING ROOT GROWTH AND GROWTH OF MYCORRHIZA

(71) Applicant: SweTree Technologies AB, Umeå (SE)

(72) Inventors: Torgny Näsholm, Holmsund (SE); Henrik Svennerstam, Umeå (SE)

(73) Assignee: SWETREE TECHNOLOGIES AB, Umea (SE)

( * ) Notice: Subject to any disclaimer, the term of this patent is extended or adjusted under 35 U.S.C. 154(b) by 0 days.

(21) Appl. No.: 14/248,529

(22) Filed: Apr. 9, 2014

(65) Prior Publication Data

US 2014/0245800 A1    Sep. 4, 2014

Related U.S. Application Data

(63) Continuation of application No. 12/809,571, filed as application No. PCT/SE2008/051537 on Dec. 19, 2008, now abandoned.

(60) Provisional application No. 61/015,204, filed on Dec. 20, 2007.

(30) Foreign Application Priority Data

Dec. 20, 2007 (SE) ...................... 0702843

(51) Int. Cl.

| C05F 11/00 | (2006.01) |
|---|---|
| C05C 1/00 | (2006.01) |
| C05C 5/00 | (2006.01) |
| C05C 11/00 | (2006.01) |
| A01N 37/44 | (2006.01) |

(Continued)

(52) U.S. Cl.
CPC ............... *C05C 11/00* (2013.01); *A01N 37/44* (2013.01); *A01N 47/44* (2013.01); *C05C 1/00* (2013.01); *C05C 5/00* (2013.01); *C05F 11/00* (2013.01); *C05F 11/10* (2013.01); *Y02P 60/218* (2015.11)

(58) Field of Classification Search
None
See application file for complete search history.

(56) References Cited

U.S. PATENT DOCUMENTS

| 4,945,059 A | 7/1990 | Okii et al. |
| 6,241,795 B1 * | 6/2001 | Svec et al. ..................... 71/11 |
| 7,381,237 B2 | 6/2008 | Nasholm et al. |

(Continued)

FOREIGN PATENT DOCUMENTS

| AU | 659115 B2 | 5/1995 |
| DE | 279165 A1 | 5/1990 |

(Continued)

OTHER PUBLICATIONS

Office Action received for Australian Patent Application No. 2008341177, issued on Feb. 13, 2014, 5 pages.

(Continued)

*Primary Examiner* — Wayne Langel
(74) *Attorney, Agent, or Firm* — Rothwell, Figg, Ernst & Manbeck, P.C.

(57) ABSTRACT

The present invention provides a method of using a fertilizer, comprising an amino acid selected from the group of L-glutamine, L-asparagine and L-arginine as major nitrogen source, optionally together with inorganic nitrogen and/or a suitable preservative, for stimulating root growth, inducing more fine roots, increase the number of root tips and/or for stimulating mycorrhiza development.

19 Claims, 10 Drawing Sheets

Figure 1:
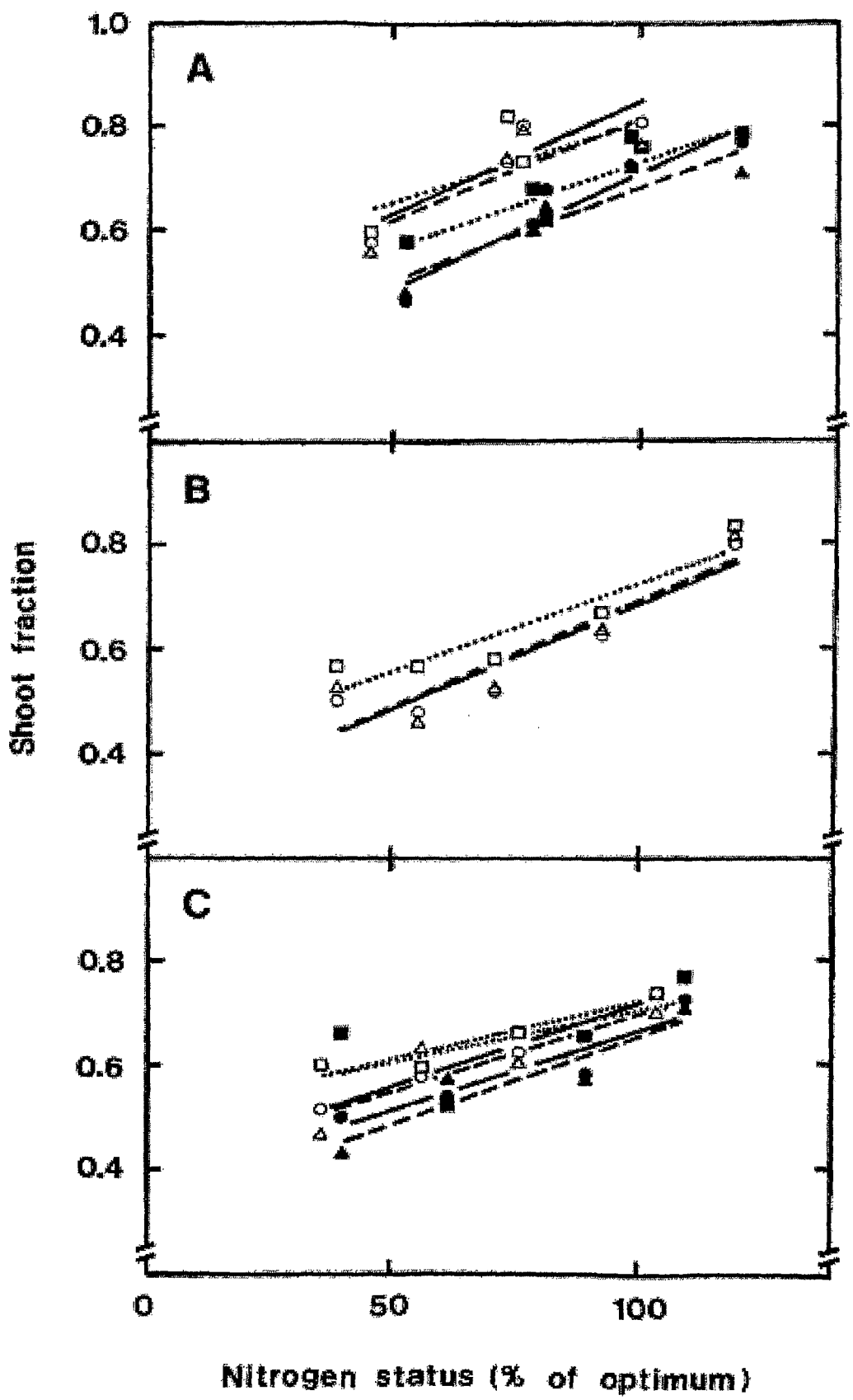

(51) Int. Cl.
*A01N 47/44* (2006.01)
*C05F 11/10* (2006.01)

(56) References Cited

U.S. PATENT DOCUMENTS

| | | | |
|---|---|---|---|
| 7,776,124 B2* | 8/2010 | Binder et al. | 71/6 |
| 7,811,352 B2 | 10/2010 | Binder et al. | |
| 7,892,313 B2 | 2/2011 | Näsholm et al. | |
| 2004/0025554 A1* | 2/2004 | Nasholm et al. | 71/27 |
| 2006/0178269 A1 | 8/2006 | Medina-Vega | |
| 2009/0031775 A1* | 2/2009 | Bevans et al. | 71/23 |

FOREIGN PATENT DOCUMENTS

| | | | |
|---|---|---|---|
| EP | 1284945 B1 | 3/2005 | |
| JP | 58-170703 | * | 10/1983 |
| JP | 2-255604 A | 10/1990 | |
| JP | 3-201914 A | 9/1991 | |
| JP | 6-256125 A | 9/1994 | |
| JP | 11-239499 A | 9/1999 | |
| JP | 3-82474 U | 12/2001 | |
| JP | 2002-159222 A | 6/2002 | |
| JP | 2003-9666 A | 1/2003 | |
| JP | 2003-12389 A | 1/2003 | |
| JP | 2003-73210 A | 3/2003 | |
| JP | 2005-229917 A | 9/2005 | |
| JP | 2006-121975 A | 5/2006 | |
| RU | 2016510 C1 | 7/1994 | |
| WO | 98/19533 A1 | 5/1998 | |
| WO | 01/87804 A1 | 11/2001 | |

OTHER PUBLICATIONS

Office Action received for Japanese Patent Application No. 2010-539389, mailed on Mar. 17, 2014, 6 pages. (3 pages of English Translation and 3 pages of Official copy).
"CABA abstract: 42904", 1990.
"HCAPLUS abstract: 388236", 2001.
"HCAPLUS abstract: 28848", 1955.
"Hcaplus abstract: 37855", 1980.
Office Action received for Australian Patent Application No. 2008341177, issued on Apr. 8, 2013, 4 pages.
Office Action received for Chinese Patent Application No. 200880121502.2, issued on Aug. 19, 2013, 16 pages.
Office Action received for Chinese Patent Application No. 200880121502.2, issued on Oct. 29, 2012, 16 pages.
Office Action received for Chilean Patent Application No. 3729-2007, received on Aug. 12, 2013, 11 pages.
Office Action received for Chilean Patent Application No. 3729-2007, received on Oct. 25, 2012, 12 pages.
Extended European Search Report received for European Patent Application No. 08864797.9 mailed on Feb. 6, 2013, 7 pages.
International Preliminary Report on Patentability received for PCT Patent Application No. PCT/SE2008/051537, mailed on Jun. 22, 2010, 11 pages.
International Search Report and Written Opinion received for PCT Application No. PCT/SE2008/051537, mailed on Mar. 31, 2009, 15 pages.
Office Action received for Japanese Patent Application No. 2010-539389, mailed on May 7, 2013, 9 pages.
Non Final Office Action received for U.S. Appl. No. 12/809,571, mailed on Dec. 11, 2013, 17 pages.
Non Final Office Action received for U.S. Appl. No. 12/809,571, mailed on Oct. 9, 2012, 5 pages.
Chen et al., "Glutathione Reduces the Inhibition of Rice Seedling Root Growth Caused by Cadmium", Plant Growth Regulation, vol. 16 No. 3, 1995, pp. 249-252.
Chen et al., "Utilisation of Organic Nitrogen and Phosphorus Sources by Mycorrhizal Endophytes of Woollsia Pungens (*Cav.*) F. Muell. (*Epacridaceae*)", Mycorrhiza, vol. 8 No. 4, 1999, pp. 181-187.
Dupre et al., "Effect of Nitrogen and Phosphorus on Mycorrhiza Formation on Quercus Pubescens Willd. By Tuber Melanosporum Vitt. under Controlled Conditions", Colloques—Institut National de la Recherche Agronomique, vol. 13, (abstract only), 1982, pp. 147-153.
Hepper et al., "Hyphal Growth From Spores of the Mycorrhizal Fungus Glomus Caledonius: Effect of Amino Acids", Soil Biology and Biochemistry, vol. 15, No. 1, (abstract only), 1983, pp. 55-58.
Ingestad et al., "The Influence of Plant Nutrition on Biomass Allocation", Ecological Applications, vol. 1, No. 2, May 1991, pp. 168-174.
Lipson et al., "The Unexpected Versatility of Plants: Organic Nitrogen Use and Availability in Terrestrial Ecosystems", Oecologia, vol. 128, 2001, pp. 305-316.
Lucas et al., "Soil Microbial Communities and Extracellular Enzyme Activity in the New Jersey Pinelands", Soil Biology and Biochemistry, vol. 39, No. 10, (abstract only), 2007, pp. 2508-2519.
Murai et al., "Effects of Amino Acids on in vitro Rooting of Japanese Plum (*Prunus salicina* Lindl.)", Plant Tissue Culture, vol. 13, No. 3, Dec. 1996, pp. 321-323.
Plassard et al., "Differential Effects of Mineral and Organic N Sources, and of Ectomycorrhizal Infection by Hebeloma Culindrosporum, on Growth and N Utilization in Pinus Pinasterc", Plant, Cell and Environment, vol. 23, No. 11, 2000, pp. 1195-1205.
Raab et al., "Non-mycorrhizal Uptake of Amino Acids by Roots of the Alpine Sedge Kobresia Myosauroides: Implications for the Alpine Nitrogen Cycle", Oecologia, vol. 108, No. 3, 1996, pp. 488-494.
Rudawska, "Effect of Various Organic Sources of Nitrogen on the Growth of Mycelium and Content of Auxin and Cytokinin in Cultures of Some Mucorrhizal Fungi", Acta Physiologiae Plantarum, vol. 4, No. 1-2, (abstract only), 1982, pp. 11-20.
Smith et al., "Mycorrhizal Symbiosis", Second Edition, Academic press, 1997.
Xueping et al., "Effects of Exogenous Amino Acids on the Contents of Amino Acids in Tobacco Leaves", Agricultural Sciences in China, vol. 4, No. 2, (abstract only), 2005, pp. 113-117.

* cited by examiner

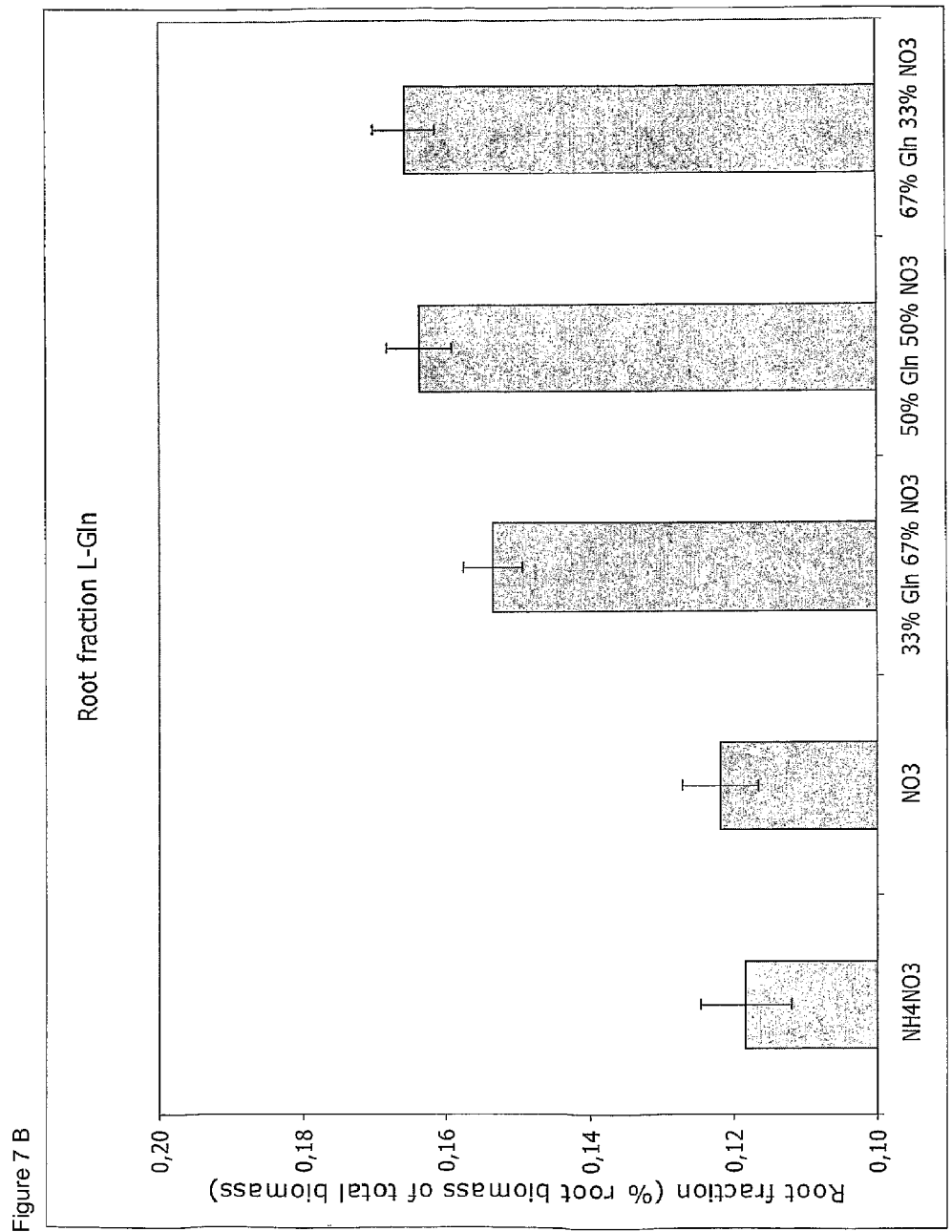

USE OF A FERTILIZER CONTAINING L-AMINO ACID FOR IMPROVING ROOT GROWTH AND GROWTH OF MYCORRHIZA

CROSS REFERENCE TO RELATED APPLICATIONS

This application is a Continuation of U.S. patent application Ser. No. 12/809,571, filed Jun. 30, 2011, which is a U.S. National Phase patent application of PCT/SE2008/051537, filed Dec. 19, 2008, which claims priority to Swedish patent application Serial No. SE 0702843-4, filed Dec. 20, 2007, and U.S. provisional patent application Ser. No. 61/015,204, filed Dec. 20, 2007, all of which are hereby incorporated by reference in the present disclosure in their entirety.

The present invention relates to the use of a fertilizer affecting plant biomass allocation. More specifically, the fertilizer is able to stimulate root growth, fine root development, increase the number of root tips and mycorrhiza development. Thus, the invention provides methods for using the fertilizer in order to stimulate root growth, fine root development, increase the number of root tips and mycorrhiza development. Furthermore, the invention provides a method for using the fertilizer for modulation of the root fraction of the biomass.

TECHNICAL BACKGROUND

Allocation of growth between shoots and roots is a major process by which plant acclimates to various environmental conditions. It is well-known that nitrogen supply is a major determinant of this process. At high nitrogen supply, growth of above ground parts is stimulated relative to that of structures below ground, while at low nitrogen supply, root growth is enhanced (FIG. 1). This strong dependence of allocation on nitrogen supply has been demonstrated for a number of plant species and for a range of different nitrogen addition rates. Nitrogen supply will, therefore, alter the structure of plants and hence, plant resistance to various stresses such as wind and drought.

The general idea of nitrogen effects on plant biomass allocation is that at higher rates of N supply, plants sense a decreased need for nitrogen uptake and hence for root growth but an increase need for carbon uptake and hence for shoot growth. This simple relationship between nitrogen and carbon access and biomass allocation may be regulated through external cues and through sensing the levels of critical metabolites such as sucrose and glutamine within the plant.

During plant cultivation, ample supply of nutrients and in particular of nitrogen is a prerequisite for good growth. As described above, high amounts of nutrients generally stimulate growth of above ground parts more than of belowground parts and thus commercially cultivated plants, because of ample supply of nutrients; have often a high and unbalanced shoot mass fraction. There are, however, a number of situations in which plants with a high root mass fraction are superior to those with a low root mass fraction. Typically, plants precultivated for plantation outdoors or plants raised from cuttings should have a high root mass fraction to enable efficient establishment following plantation. Thus, in all situations where plants or seedlings are precultivated for later plantation, a high root mass fraction will be a positive factor for growth and establishment.

From what is described above it can be concluded that efficient cultivation of plants is incompatible with an optimal plant allocation pattern. The need for high growth rates during cultivation can only be achieved through application of high amounts of N which in turn stimulates shoot growth more than root growth and thus leads to an imbalanced allocation. Ideally, plant cultivation conditions should allow for efficient growth but still have a high root mass fraction. With current cultivation methods, this cannot be achieved.

During the last decade, a number of studies have shown that organic nitrogen compounds and in particular amino acids are important nitrogen sources for plants. These studies have demonstrated the occurrence of amino acid uptake in both field and laboratory settings and for a range of different plant species, including mycorrhizal and non-mycorrhizal plants and also for a number of crop plants, e.g. wheat, corn, barley (Lipson and Näsholm 2001). Several studies have demonstrated how absorbed organic nitrogen compounds are metabolized following root uptake and also shown how nitrogen from such sources is incorporated into proteins. Moreover, a number of studies have demonstrated that plants may use organic nitrogen compounds for growth. Thus, it is now widely accepted that organic nitrogen compounds such as amino acid may function as nitrogen sources for plants.

It is generally held that all nitrogen forms following absorption (i.e. both inorganic and organic nitrogen forms) are metabolized and thus forms a common nitrogen pool within the plant, which is available for plant growth. Thus, according to this general knowledge, all nitrogen forms absorbed by a plant root would be part of a common nitrogen pool and therefore all forms of nitrogen absorbed by a plant root should be spread evenly within the plant.

It is known from in vitro studies in RU2016510 that protein hydrolysate containing a mix of amino acids have been used for stimulating rooting of callus and plant growth in hydroponic processes. Nothing is taught about the use of a pure natural L-amino acid for stimulating root growth of plants in this patent.

AU659115 discloses a process to manufacture and the use of a fertilizer containing natural occurring L-amino acids, which are produced by enzymatic digestion of at least two proteolytic enzymes. AU659115 only discuss the advantage of using small molecules (amino acids) as nutrients to enhance the up take. Nothing is taught about the use of a pure natural L-amino acid for stimulating root growth of plants. Furthermore, nothing is taught about the simultaneously development of mycorrhiza at the same time as it stimulates growth of the whole plant in these two patents.

EP 1,284,945 describes a fertilizer suitable for plants in particular coniferous trees. An advantageous feature of the fertilizer is that it is substantially stationary thereby minimizing undesirable nitrogen leakage to the environment. The main nitrogen source of the fertilizer is the L-form of a basic amino acid or its salt, in particular L-arginine. This document is completely silent regarding stimulation of root growth and mycorrhiza development.

Thus, there is still a need for a nitrogen-containing fertilizer having the ability of stimulating root growth and/or mycorrhiza development at the same time as it stimulates growth of the entire plant.

It has been observed that plant of different species grow slowly or have slow start when planted outdoors in forest regeneration.

It has further been speculated that a high root mass fraction and a high number of root tips or fine roots would help these small plants to efficiently establish in the new growth environment In summary there is a need of a fertilizer that can be used to increase the root mass fraction, the number of roots, root tips and the number of fine roots on plants but without compromising growth of the whole plant.

SUMMARY OF THE INVENTION

It has now surprisingly been shown that it is possible to provide a fertilizer capable of inducing and stimulating root growth as well as development of mycorrhiza at the same time as it stimulates growth of the whole plant.

The present invention provides a method of using a fertilizer characterized in that it comprises a naturally occurring L-amino acid as nitrogen source for stimulating root growth.

Further this invention provides a method of using a fertilizer characterized in that it comprises a naturally occurring L-amino acid as a nitrogen source for stimulating mycorrhiza development.

The present invention provides further a method of using a fertilizer, which comprises an amino acid selected from the group of L-glutamine, L-asparagine and L-arginine as major nitrogen source, optionally together with a suitable preservative, for stimulating root growth and/or for stimulating mycorrhiza development.

Further, it is disclosed the use of a fertilizer comprising a naturally occurring L-amino acid as a major nitrogen source for stimulating root growth and/or for stimulating mycorrhiza development.

Further, it is disclosed the use of a fertilizer comprising a naturally occurring L-amino acid, in particular chosen from the group of L-arginine, L-asparagine and L-glutamine as a nitrogen source, for stimulating root growth and/or for stimulating mycorrhiza development.

Further, it is disclosed the use of a fertilizer wherein in that the fertiliser also comprises inorganic nitrogen.

Further, the L-amino acid is chosen from the group of L-arginine, L-asparagine, glycine, L-glutamic acid and L-glutamine.

Further, it is disclosed the use of a fertilizer wherein at least 30% (wt) of the nitrogen source therein, preferably at least 70% (wt) of the nitrogen source therein, preferably at least 85% (wt), and most preferably at least 90% (wt), is a L-amino acid and the other nitrogen source is an inorganic nitrogen compound, such that the stimulation of the root and shoot growth is related to the ratio between the L-amino acid and the inorganic nitrogen compound. In some examples the L-amino acid is L-arginine and/or L-glutamine.

It is also disclosed a method for using the fertilizer for modulation of the root fraction of the biomass.

Furthermore, it is disclosed that the higher fraction of the nitrogen source that is a L-amino acid, the higher the root fraction is of the biomass, i.e. more L-amino acid in the used fertilizer will give more roots, more fine roots and many more root tips that can help the plants when planted outdoors.

Further, it is disclosed the use of a fertilizer comprising a naturally occurring L-amino acid wherein the fertilizer also contains a suitable preservative.

Further, it is disclosed the use of a fertilizer comprising a naturally occurring L-amino acid wherein the preservative is selected from the group of a preservatives such as benzoic acid, acetic acid, salicylic acid, propionic acid, sorbic acid, citric acid, or their salts and alexin plus.

Further, it is disclosed the use of a fertilizer comprising a naturally occurring L-amino acid wherein the fertilizer is solid or is a solution.

The present invention also provides a method of using a fertilizer, comprising an amino acid selected from the group of L-glutamine, L-asparagine and L-arginine as major nitrogen source, optionally together with a suitable preservative, for stimulating root growth.

The present invention also provides a fertilizer comprising a naturally occurring amino acid. The naturally occurring amino acids that can be used in the fertilizer of the present invention are glycine, L-alanine, L-valine, L-leucine, L-isoleucine, L-serine, L-cysteine, L-threonine, L-methionine, proline, L-aspatic acid, L-asparagine, L-glutamic acid, L-glutamine, L-lysine, L-arginine, L-histidine, L-phenylalanine, L-tyrosine and L-tryptophan. In a preferred embodiment, the amino acid is chosen from the group of glycine, L-glutamic acid, L-glutamine and L-agrinine. Most preferably, the amino acid is chosen from the group of L-arginine and L-glutamine as major nitrogen source. The fertilizer also contains a suitable preservative.

Preferably at least 30% (wt) of the nitrogen source therein, preferably at least 70% (wt), preferably at least 85% (wt), and most preferably at least 90% (wt), is a natural amino acid, such as L-arginine and/or L-glutamine.

Further, the use of a fertilizer could be characterized in that the fertiliser also comprises an inorganic nitrogen compound such as nitrate or ammonium for simultaneously stimulating root and shoot growth.

Further, examples of inorganic nitrogen compounds are nitrate, and ammonium.

Preferably, the preservative is selected from the group of a benzoate such as potassium benzoate, acetic acid, salicylic acid, propionic acid, sorbic acid, citric acid, and alexin plus. A typical concentration of potassium benzoate amounts to 400-3000 ppm, preferably 600-2000 ppm and most preferably 800-1200 ppm. A typical concentration of acetic acid amounts to 2000-10000 ppm, preferably 4000-8000 ppm, and most preferably 5000-7000 ppm. A typical concentration of salicylic acid amounts to 250-2000 ppm, preferably 500-1500 ppm, and most preferably 800-1200 ppm. A typical concentration of propionic acid amounts to 2000-10000 ppm, preferably 4000-8000 ppm, and most preferably 5000-7000 ppm. A typical concentration of sorbic acid amounts to 2500-20000 ppm, preferably 5000-15000 ppm, and most preferably 7500-12500 ppm. A typical concentration of Alexin plus (Citrox Ltd, United Kingdom) amounts to 10000-50000 ppm, preferably 20000-40000 ppm, and most preferably 25000-35000 ppm.

Preferably, the fertilizer contains an additional component selected from the group of magnesium sulphate, potassium sulphate, potassium dihydrogen phosphate, potassium chloride, and trace elements, wherein the trace elements are selected from the group of Fe, Mn, Cu, Zn, B and Mo. Typically, the fertilizer may comprise 2-5% (wt), preferably 3-4% (wt) magnesium sulphate, 1-3% (wt), preferably 2-3% (wt) potassium sulphate, preferably 4-5% (wt) potassium dihydrogenphosphate, 2-5% (wt), preferably 3-4% (wt) potassium chloride. Preferably, the trace elements are added as a special trace element composition. An example of such a composition is Micro+, available from LMI AB, Sweden. Typically, the amount of Micro+ in the fertilizer is 4-5% (wt).

DETAILED DESCRIPTION OF THE INVENTION

Figure 2:
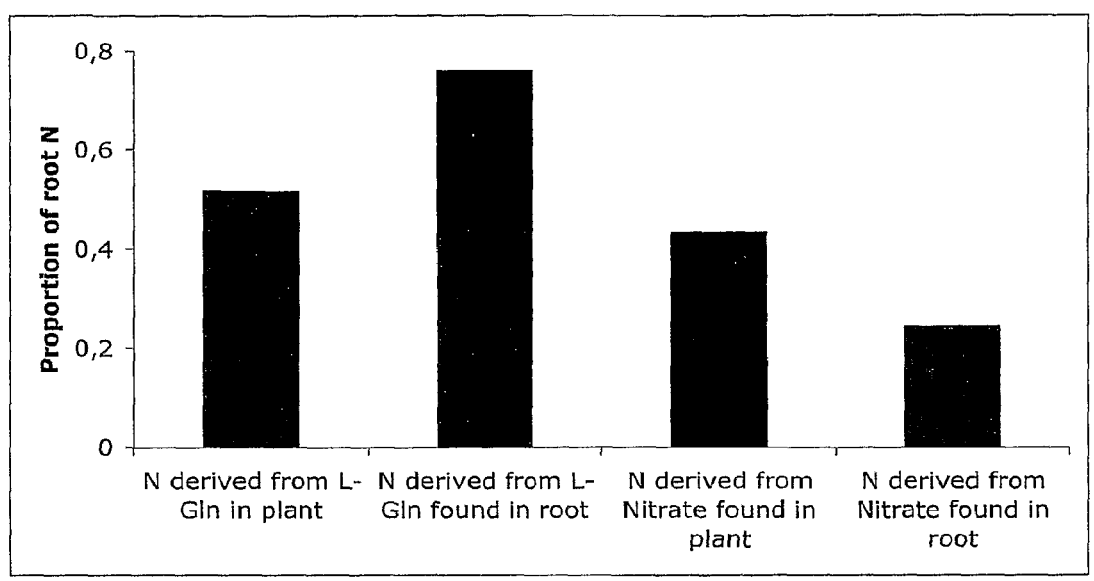

The present invention will now be further described with reference to the enclosed figures, in which:

FIG. 1 shows the effect of plant nitrogen status (% of N concentration optimal for growth) on plant biomass allocation expressed as fraction of shoot biomass of total biomass. A, B and C refers to data from experiments with *Picea abies, Pinus contorta* and *Pinus sylvestris* respectively (from Ingestad & Ågren 1986);

FIG. 2 reveals the content of nitrogen derived from uptake of L-Glutamine and nitrate found in the whole plant and in the roots of seedlings of *Arabidopsis thaliana*. The graph shows that absorbed L-Glutamine is preferentially used for root growth.

Figure 3:
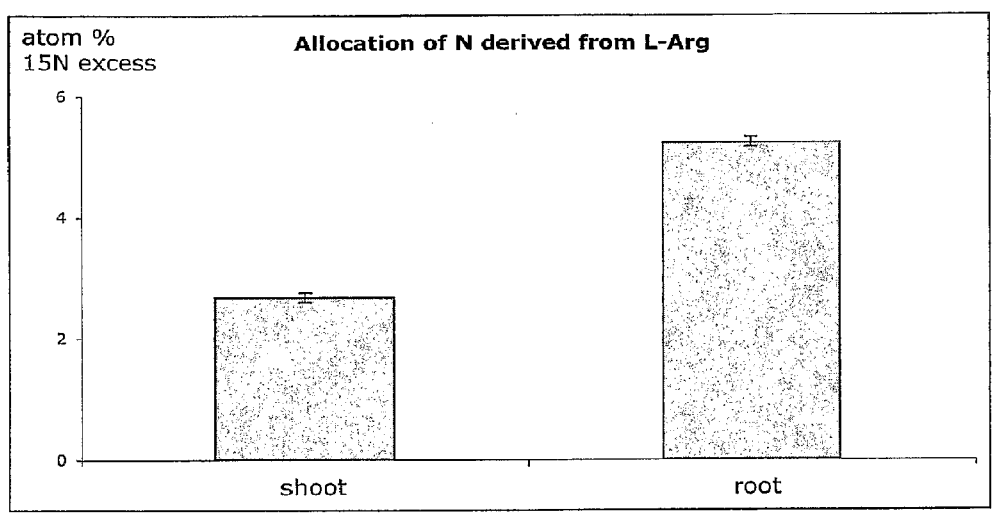
Figure 4A:
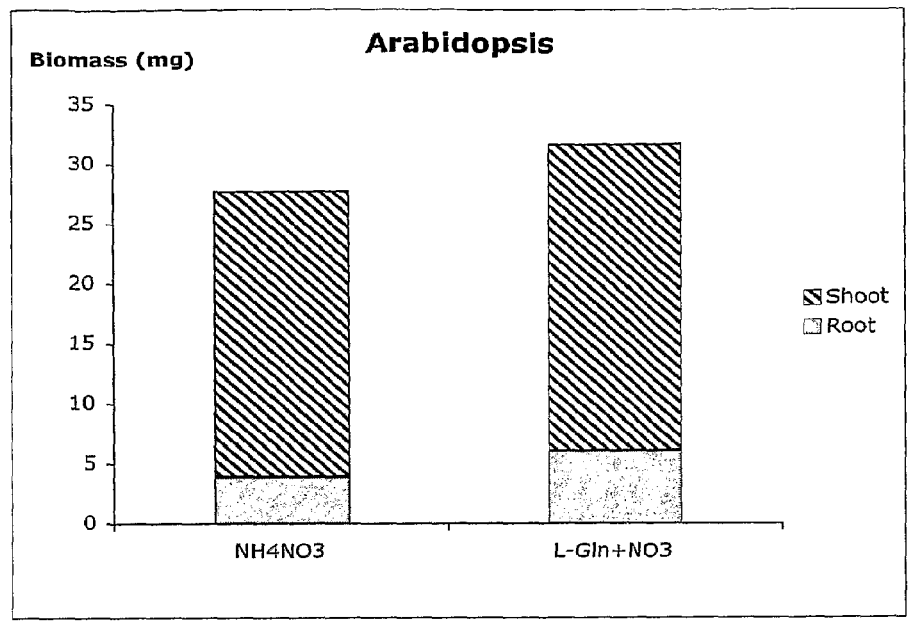
Figure 4B:
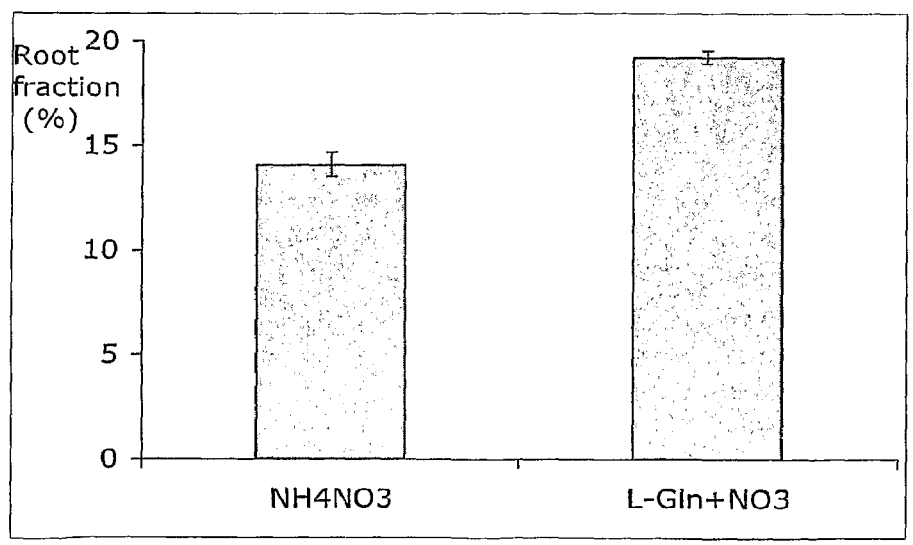
Figure 5A:
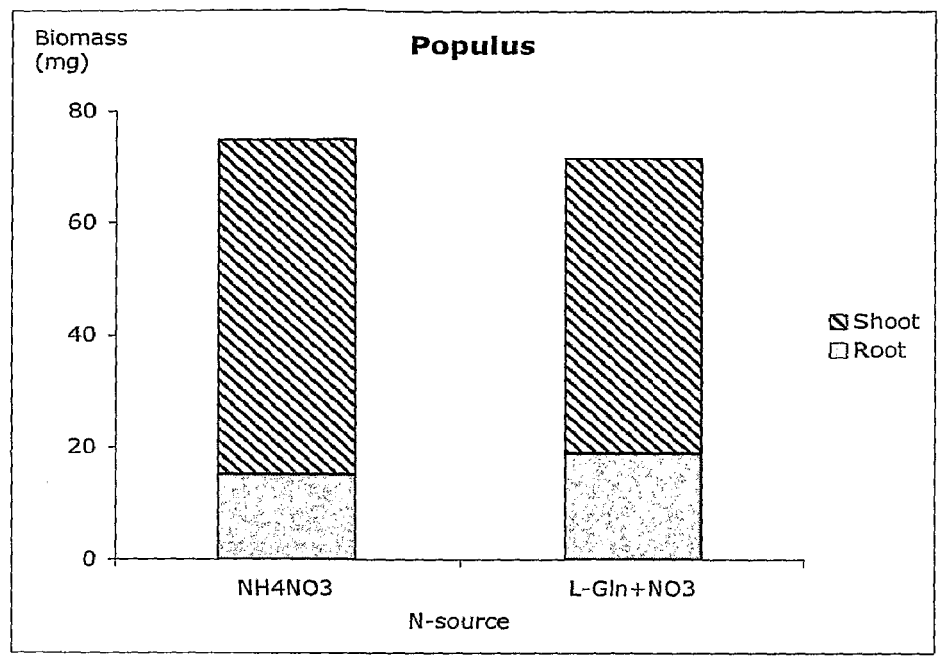
Figure 5B:
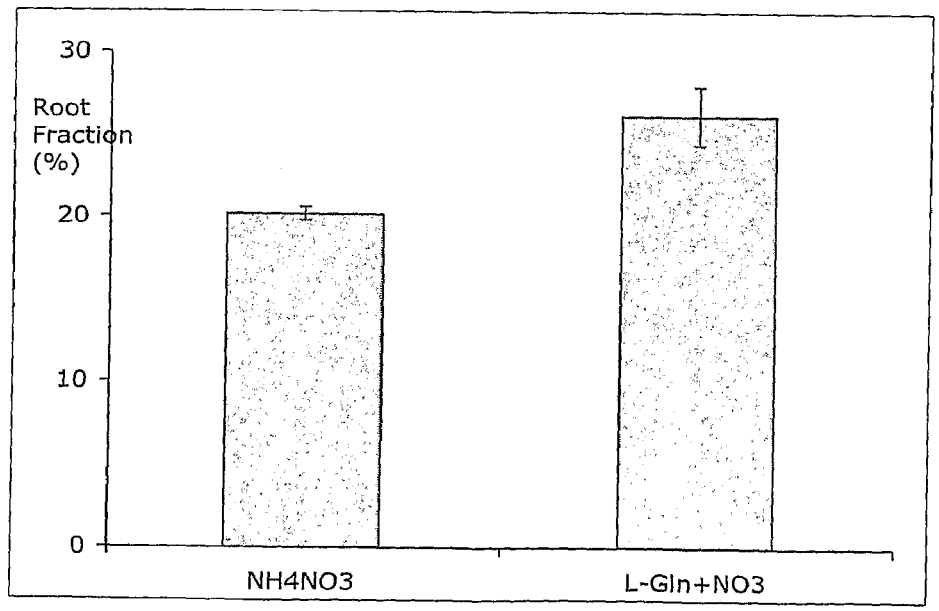

FIG. 3 discloses allocation of nitrogen derived from uptake of L-arginine. Plants grown on 3 mM nitrate were supplied with small amounts (30 μM) of N-15 labelled L-Arginine. Following 21 days of cultivation, plants were harvested, roots and shoots were separated and subsequently analysed for their content of N-15. The amount of N-15, expressed as atom% excess, in the two plant parts shows that nitrogen from L-Arginine is preferentially used for root growth;

FIGS. 4A and 4B shows biomass of *Arabidopsis thaliana* plants and allocation of biomass to roots and shoots of plants cultivated either on ammoniumnitrate or L-Glutamine and nitrate (4A) and the root mass fraction of plant cultivated either on ammonium nitrate or L-Glutamine and nitrate (4B);

FIGS. 5A and 5B reveals biomass of *Populus* plants and allocation of biomass to roots and shoots of plants cultivated either on ammoniumnitrate or L-Glutamine and nitrate (5A) and the root mass fraction of plant cultivated either on ammonium nitrate or L-Glutamine and nitrate (5B).

Figure 6:
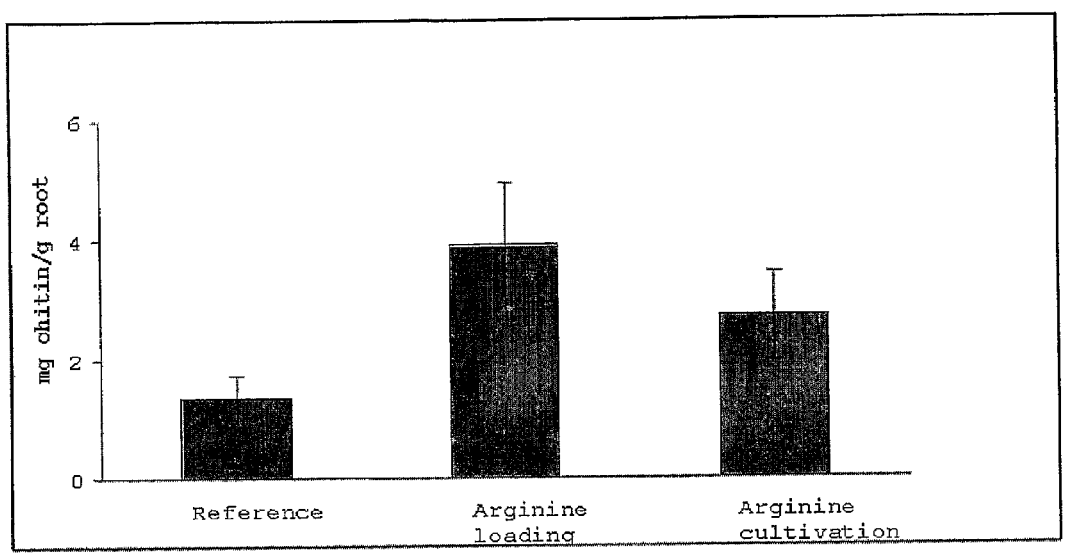

FIG. 6 discloses the chitin content of Scots pine roots. Plants were either cultivated with a mixture of ammonium and nitrate as nitrogen sources (reference), cultivated with ammonium and nitrate but supplied with arginine after the last fertilization event in autumn (arginine loaded) or cultivated with arginine as the sole source of nitrogen throughout the growth season (arginine cultivated). Chitin is part of the fungal cell wall and thus indicates the fraction of mycorrhiza in the total root system.

Figure 7:
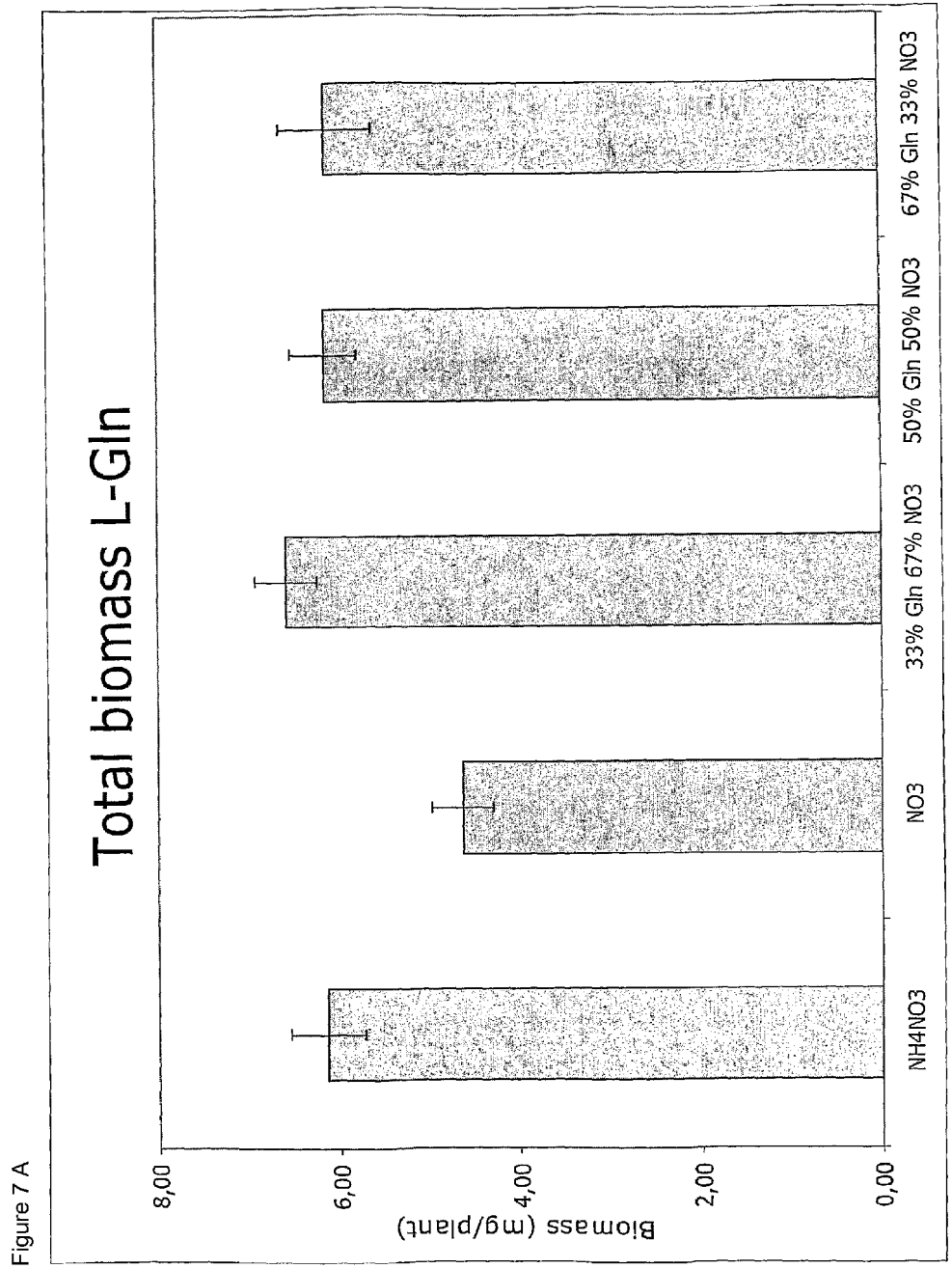

FIG. 7 disclose the effect of various proportions of L-Glutamine (Gln) on total biomass production (FIG. 7A) and production of roots (FIG. 7B).

Figure 8:
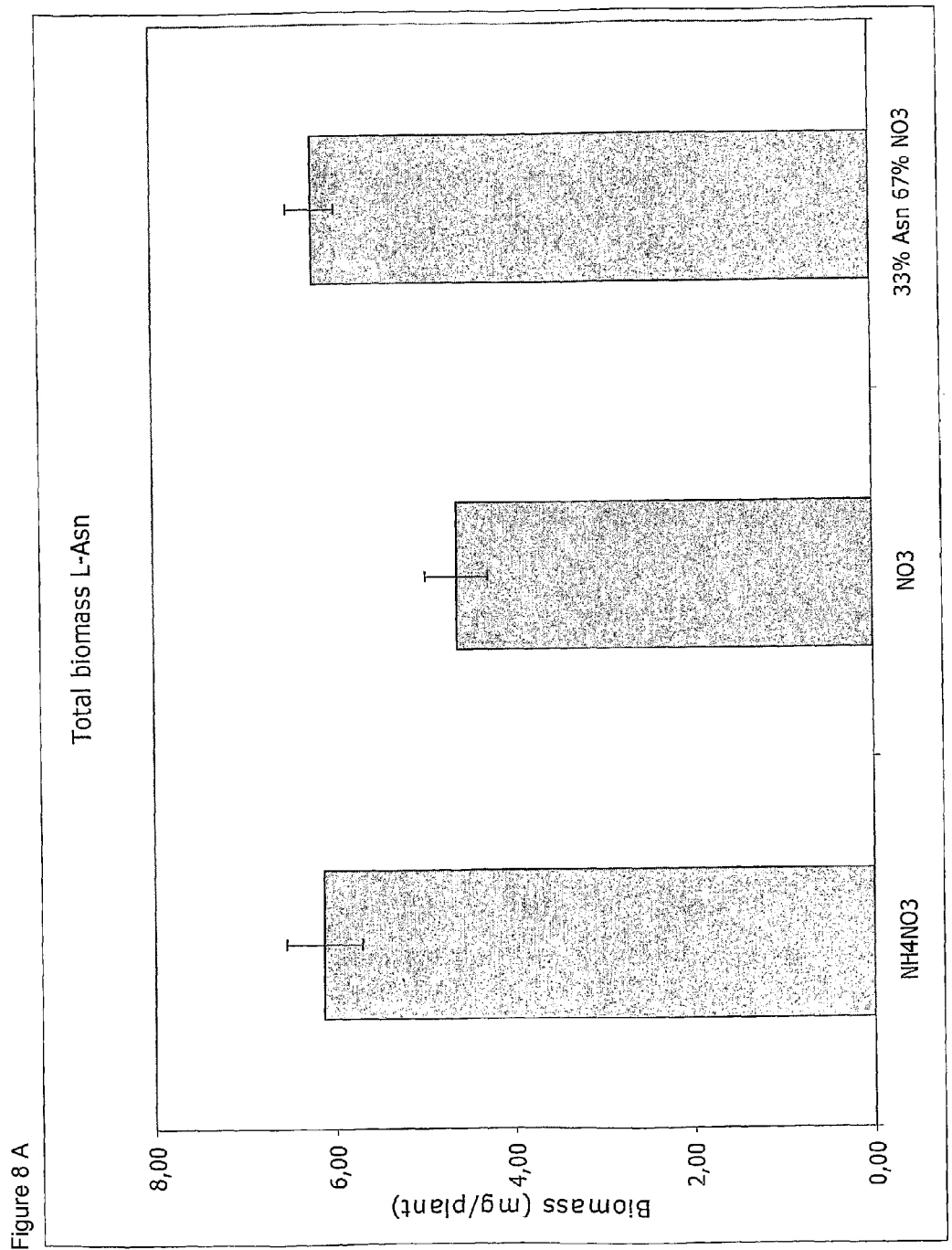
Figure 8:
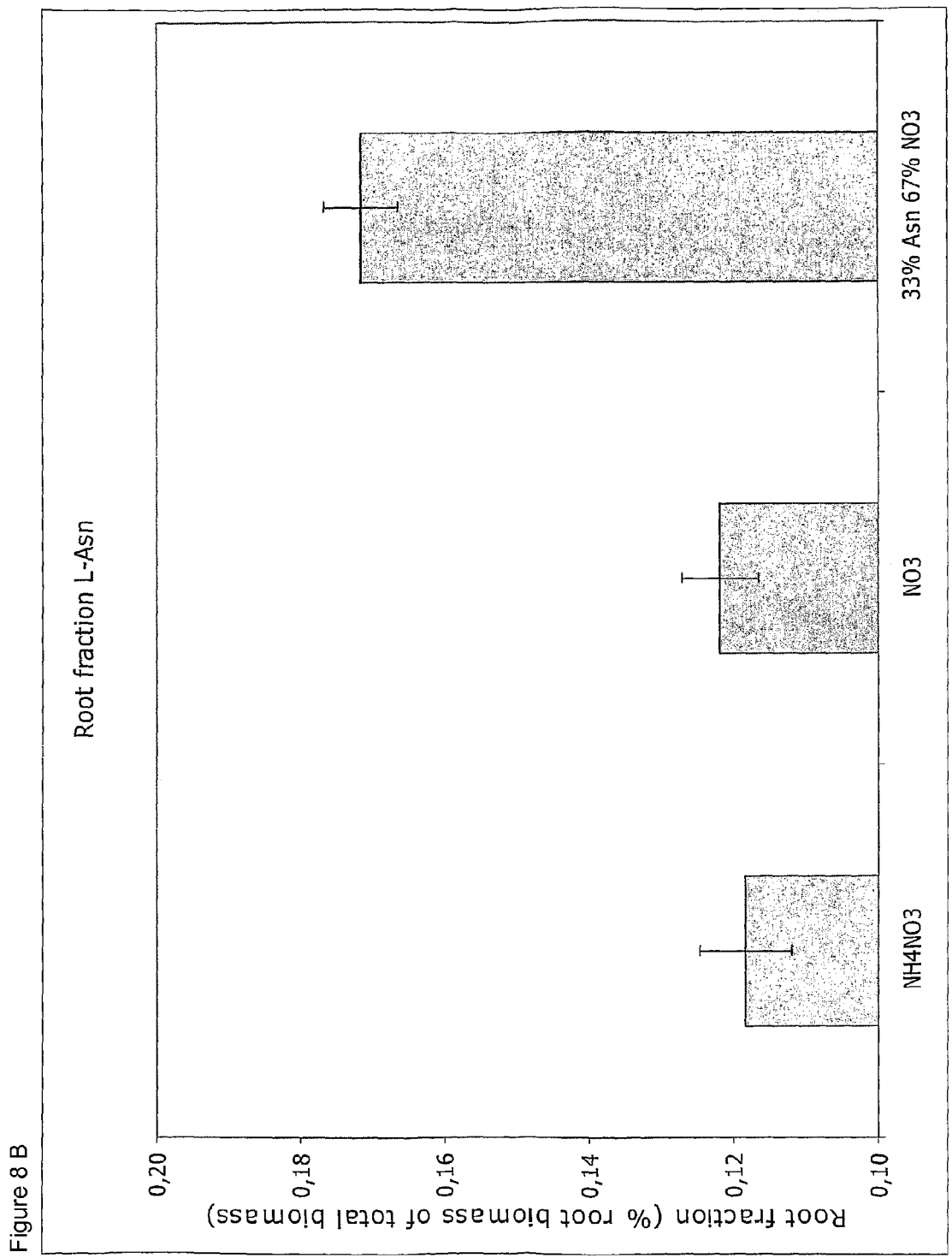

FIG. 8 disclose the effect of L-Asparagine (Asn) on total biomass production (FIG. 8A) and production of roots (FIG. 8B).

Through a series of experiments, the inventors have discovered that plants supplied with a mixture of organic and inorganic nitrogen forms will distribute nitrogen derived from these different forms unevenly so that a greater share of plant nitrogen derived from organic nitrogen forms are found in roots than in other plant parts. In FIG. 2, results from an experiment in which small *Arabidposis thaliana* plants were supplied either with a mixture of ammonium and nitrate or a mixture of L-Glutamine and nitrate are shown. FIG. 2 shows that for the whole plant, c. 50% of nitrogen is derived from uptake of L-Glutamine while c. 75% of root nitrogen is derived from this nitrogen form. Conversely, c. 45% of whole plant nitrogen is derived from uptake of nitrate while only c. 25% of root nitrogen is derived from uptake of this nitrogen form. Similarly, when *A. thaliana* plants were cultivated on nitrate and only small amounts of L-Arginine was added to the growth media (FIG. 3), a higher fraction of nitrogen derived from L-Arginine was found in roots compared to in shoots. These experiments thus show that plants supplied with a mixture of nitrogen forms use organic nitrogen primarily for root growth.

To our surprise we also found that root growth of *A. thaliana* plants supplied with a mixture of organic and inorganic nitrogen (in this case L-Glutamine and nitrate) was readily stimulated compared to that achieved on a mixture of ammonium and nitrate (FIGS. 4A and 4B). In a second experiment, the effect of different mixtures of nitrogen sources was tested on *Populus* seedlings (FIGS. 5A and 5B). As for *A. thaliana*, a significant increase in root mass fraction was found for plants supplied with L-Glutamine and nitrate compared to those supplied with ammonium and nitrate. According to these data, plant growth was similar or better for plants supplied with a mixture of organic and inorganic nitrogen forms compared to those given only inorganic forms. At the same time, the root mass fraction was significantly higher for plants supplied with a mixture of organic and inorganic nitrogen. This shows that, at equal or better growth, a higher root mass fraction can be achieved through cultivating plants on organic nitrogen or mixtures between inorganic and organic nitrogen compared to when plants are supplied with inorganic nitrogen only.

The current invention relates to the possibility to adjust plant biomass allocation to roots through use of specific amino acids as fertilizers during plant cultivation. Mixtures in which specific amino acids forms a dominant part of the nitrogen in the fertilizers can thus be used to specifically increase root growth of plants and thus increase the root mass fraction of the produced plant. Mixtures with a dominance of inorganic nitrogen forms can, accordingly, be used to specifically increase the shoot mass fraction of the plant.

Many plants form symbioses with fungi, called mycorrhiza. It is well known that mycorrhizas develop poorly on plants given high amounts of nutrients (Smith, S. E., and D. J. Read. 1997. Mycorrhizal symbiosis, $2^{nd}$ Edition. Academic Press, New York, N.Y., USA.). Mycorrhizas are known to be beneficial for plants and promote plant uptake of mineral nutrients and of water as well as to protect plants from various pathogenes. Thus, cultivation of plants that, under natural conditions form mycorrhiza, should enable such symbioses to form. As stated above, however, high rates of nutrient addition may severely hamper or may not allow the development of mycorrhiza on cultivated plants.

Several of the fungal species that form mycorrhiza are also known to form edible fruit bodies (mushrooms). However, production of fruitbodies will also be hampered by high rates of nutrient additions, i.e. the conditions that are used to stimulate plant growth.

The above-mentioned obvious contradiction between efficient cultivation of plants and the simultaneous development of mycorrhiza and of edible mushrooms is to a significant degree dependent on the addition of large amounts of nitrogen in the fertilizer.

Furthermore it was very unexpected that the number of root tips and the number of fine roots increased to such high levels that it helped the plantlets to survive the first period after plantation.

The examples relates to the use of one amino acid and not two or more. The fertilizer is not intended for invitro use and not for cut flowers.

An ideal fertilizer should hence stimulate not only plant growth but also growth of symbiotic fungi forming mycorrhiza. Furthermore, an ideal fertilizer should also allow for production of fungal fruit bodies. To our surprise, we found that plants cultivated on amino acids both displayed a high growth rate and vigorous development of mycorrhiza. The stimulation of mycorrhiza formation was found both on plants raised on amino acids and on plants raised on inorganic nitrogen sources (ammonium plus nitrate) but later supplied with amino acids.

The fertilizer may contain at least 5% (wt), at least 10% (wt), at least 15% (wt), at least 20% (wt), at least 25% (wt), at least 30% (wt), at least 35% (wt), at least 40% (wt), at least 45% (wt), at least 50% (wt), at least 55% (wt), at least 60% (wt), at least 65% (wt), at least 70% (wt), at least 75% (wt), at least 80% (wt), at least 85% (wt), at least 90% (wt), or at least 95% (wt), of the nitrogen source therein, is an L-amino acid, preferably L-arginine and/or L-glutamine.

EXPERIMENTAL PROCEDURES

Example 1

Allocation of Arginine-Nitrogen in *Arabidopsis*

The experiment was performed with wild type *Arabidopsis* on sterile agar plates containing half strength Murashige and Skoog (MS) medium (Murashige and Skoog, 1962), with 0.65% w/v agar (plant agar, Duchefa Biochemie), 0.5% w/v sucrose amended with 3 mM nitrate and 30 µM U-$^{15}$N (>98% $^{15}$N) L-Arg and buffered to pH 5.8 with 3.6 mM MES (2N-morpholinoethanesulfonic acid). Plants were grown for 19 days when 20 plants were harvested and divided into 4 replicates (i.e. each replicated consisted of 5 plants). Shoots and roots were separated; roots were rinsed and cleaned thoroughly three times in a solution of 0.5 mM CaCl$_2$ to remove adhered compounds from surfaces. Shoots and roots were dried at 60° C. overnight, weighed and homogenized. Finally, samples were analyzed using a Europe Scientific Isotope Ratio Mass Spectrometer to determine total N and $^{15}$N contents. The results are disclosed in FIG. 3.

Example 2

Allocation of Biomass and Glutamine-N in *Arabidopsis* and Poplar

Allocation experiments were performed with wild type Arabidopsis on sterile agar plates and in the case of poplar, in plastic boxes, containing the equivalent of nitrogen-free, half strength Murashige and Skoog (MS) medium (Murashige and Skoog, 1962), with 0.8% w/v agar (plant agar, Duchefa Biochemie), 0.5% w/v sucrose and pH was set to 5.8 using MES buffer. Nitrogen was added to the agar either as an equimolar mixture of NH$_4^+$ and NO$_3^-$ or as an equimolar mixture, corresponding to 50% of each of L-Gln and NO$_3^-$, both mixtures at a total rate corresponding to 3 mM N. Four labelling treatments were carried out, i.e. two for each N mixture. Thus half of the plates with the NH4NO3 mixture contained labelled NH$_4^+$, the other half contained labelled NO$_3^-$. Similarly, half of the plates with L-Gln:NO$_3^-$ mixtures contained labelled L-Gln, the other half contained labelled NO3–. For each labelling treatment, 1% of the N source was administered as $^{15}$N. Sterile filtered L-Gln was added to the agar mixture after autoclaving. Arabidopsis plants were harvested after 21 days and poplar plants after 28 days of growth. Shoots and roots were dried at 60° C. overnight, weighed and homogenized. Finally, samples were analyzed using a Europe Scientific Isotope Ratio Mass Spectrometer to determine total N and $^{15}$N contents. The amount of N derived from either of the two N sources in different plant parts (i.e. shoots and roots) were calculated from values of excess atom % 15N and total N content of the respective plant part. Root fractions of plants from the two different N mixtures were calculated as the percentage of total plant biomass present in roots. The results regarding *Arabidopsis* are disclosed in FIG. 4 and the results regarding *Populus* is disclosed in FIG. 5.

TABLE 1

The root mass fraction, i.e. the fraction of whole-plant biomass present in roots, of *Arabidopsis thaliana* and *Populus deltoides* plants grown on either a mixture of NH4+ and NO3– or a mixture of NO3– and L-Gln

| Species | NH4+ NO3– mixture | NO3– L-Gln mixture |
|---|---|---|
| *Arabidopsis* | 14.1 ± 0.6% | 19.2 ± 0.3% |
| *Populus* | 20.2 ± 0.4% | 26.2 ± 1.7% |

Example 3

Evaluation of Mycorrhiza of Scots Pine Roots

Plants were cultivated outdoors during one growth season in northern Sweden. Plants were supplied with a complex nutrient solution with either ammonium nitrate or arginine as nitrogen sources. Arginine-cultivated seedlings were fertilized once a week during the growth season (in total 50 mg N per seedling) while reference plants were fertilized 2-3 times a week (in total 71.5 mg N per seedling). Arginine-loaded seedlings received the same treatment as the reference with the exception that they also received a pulse of arginine after the last fertilization event in early autumn. The amount of arginine supplied in this pulse corresponded to 5 mg nitrogen per seedling. The average chitin content of the roots can be found in FIG. 6 and in Table 2. The values are shown as average value±standard evaluation, n=6.

TABLE 2

Chitin content of Scots pine roots

| Fertilizer | Chitin content (mg chitin/g root) Average values ± SE, n = 6 |
|---|---|
| Reference | 1.35 ± 0.39 |
| Arginine loading | 3.90 ± 1.05 |
| Arginine cultivation | 2.72 ± 1.81 |

The results clearly show that fertilization with arginine results in substantially higher content of chitin in roots which indicates mycorrhiza formation.

Example 4

Typical Fertilization Compositions

Composition A:

| Component | Amount |
|---|---|
| L-Arginine | 233140 g |
| HCl (37% aqueous solution) | 138990 g |
| Benzoate (preservative) | 1000 ppm |
| Water | 700000 g |

-continued

|  | Amount |
|---|---|
| Physical data: | |
| ξ | 1.08 |
| pH | 3.20 |
| Total weight (kg) | 1080 |
| Total volume (l) | 1000 |

Arginine and the preservative was added to and dissolved in water and subsequently, the pH was adjusted by titrating with concentrated HCl. The final pH was determined before diluting with water up to the final volume of 1000 l.

Composition B:

| Component | Amount |
|---|---|
| MgSO$_4$·7H$_2$O | 40900 g |
| K$_2$SO$_4$ | 27270 g |
| KH$_2$PO$_4$ | 54530 g |
| KCl | 40900 g |
| Arginine | 233140 g |
| Micro+ | 55820 g |
| HCl (37% aqueous solution) | 147560 g |
| Benzoate (preservative) | 1000 ppm |
| Water | 640000 g |
| Physical data | |
| ξ | 1.20 |
| pH | 3.20 |
| Total weight (kg) | 1200 |
| Total volume (l) | 1000 |

The salts and the preservative were first dissolved in water and then Micro+ (trace element composition available from LMI AB, Sweden) was added. Subsequently, arginine was dissolved and pH was adjusted to 3.2 with aqueous HCl (37%). Finally, water was added up to 1000 l.

Example 5

Growth and Allocation of Biomass as Affected by Nitrogen Form in *Arabidopsis*

*Arabidposis* (*Arabidposis thaliana*) plants were grown in sterile culture for 21 days on media amended with different nitrogen sources. All media had a total nitrogen concentration of 6 mM and all other macro and micro nutrients supplied in the same amounts in each treatment.

From the experiment with the L-amino acid L-glutamine it can be seen that there is clear and unexpected correlation between the root biomass and the amount of L-glutamine added as the nitrogen source, FIGS. 7A, 7B and Table 3. Furthermore, it can be seen that the root fraction (FIG. 7B) is higher when a L-amino acid is added compared to when only inorganic nitrogen is added. This is very clear when the L-amino acid L-asparagine is added as seen in FIG. 8B and Table 4.

It could be noted that in spite of the total biomass is equal with the different nitrogen sources as seen in FIGS. 7A and 8A, the root fraction is higher then expected, as seen in FIGS. 7B and 8B.

TABLE 3

Root fraction and total biomass with L-glutamine

| N source | Root fraction | std | stderr | Total biomass | std | stderr |
|---|---|---|---|---|---|---|
| NH4NO3 | 0.12 | 0.02 | 0.01 | 6.14 | 1.12 | 0.42 |
| NO3 | 0.12 | 0.01 | 0.01 | 4.63 | 0.98 | 0.35 |
| 33% Gln 67% NO3 | 0.15 | 0.01 | 0.00 | 6.59 | 0.99 | 0.35 |
| 50% Gln 50% NO3 | 0.16 | 0.01 | 0.00 | 6.16 | 1.06 | 0.37 |
| 67% Gln 33% NO3 | 0.17 | 0.01 | 0.00 | 6.13 | 1.37 | 0.52 |

TABLE 4

Root fraction and total biomass with L-asparagine

| N source | Root fraction | std | stderr | Total biomass | std | stderr |
|---|---|---|---|---|---|---|
| NH4NO3 | 0.12 | 0.02 | 0.01 | 6.14 | 1.12 | 0.42 |
| NO3 | 0.12 | 0.01 | 0.01 | 4.63 | 0.98 | 0.35 |
| 33% Asn 67% NO3 | 0.17 | 0.01 | 0.00 | 6.23 | 0.76 | 0.27 |

The invention claimed is:

1. A method for stimulating the growth of a cultivated mycorrhizal plant, comprising the step of applying a growth effective amount of a fertilizer comprising a nitrogen source to soil having a cultivated mycorrhizal plant,
   wherein the cultivated mycorrhizal plant is a tree of a species of *Populis*, or *Picea abies*, *Pinus contorta* or *Pinus sylvestris*;
   wherein the nitrogen source comprises an inorganic compound comprising nitrogen and a naturally occurring L-amino acid;
   wherein the naturally occurring L-amino acid is L-arginine;
   wherein the growth effective amount of the fertilizer is effective to stimulate growth of the whole cultivated mycorrhizal plant;
   wherein the naturally occurring L-amino acid is present in the fertilizer in an amount effective to stimulate mycorrhiza development and to increase the root mass fraction of the cultivated mycorrhizal plant, which amount is 30% to 80%;
   whereby the growth of the whole cultivated mycorrhizal plant is stimulated and the root mass fraction of the cultivated mycorrhizal plant is increased.

2. The method of claim 1, wherein 30% to 70% by weight of the nitrogen source is the naturally occurring L-amino acid.

3. The method of claim 1, wherein 40-80% by weight of the nitrogen source is the naturally occurring L-amino acid.

4. The method of claim 1, wherein the inorganic compound containing nitrogen is nitrate or ammonium.

5. The method of claim 2, wherein the inorganic compound containing nitrogen is nitrate or ammonium.

6. The method of claim 3, wherein the inorganic compound containing nitrogen is nitrate or ammonium.

7. The method of claim 1, wherein the root mass fraction is increased by at least 25%.

8. The method of claim 7, wherein the number of roots, root tips, and the number of fine roots is increased.

9. The method of claim 1, wherein the fertilizer further comprises a preservative.

10. The method of claim 9, wherein the preservative is selected from the group consisting of benzoates, acetic acid, salicylic acid, propionic acid, sorbic acid, citric acid, and alexin plus.

11. A method for stimulating the growth of a cultivated mycorrhizal plant, comprising the step of applying a growth effective amount of a fertilizer consisting of a nitrogen source, optionally a preservative and optionally an additional component selected from the group consisting of magnesium sulphate, potassium sulphate, potassium dihydrogen phosphate, potassium chloride, trace elements and mixtures thereof, wherein the trace elements are selected from the group consisting of Fe, Mn, Cu, Zn, B, Mo and mixtures thereof to soil having a cultivated mycorrhizal plant;
- wherein the cultivated mycorrhizal plant is a tree of a species of *Populis*, or *Picea abies, Pinus contorta* or *Pinus sylvestris*;
- wherein the nitrogen source consists of an inorganic compound comprising nitrogen and a naturally occurring L-amino acid;
- wherein the naturally occurring L-amino acid is L-arginine;
- wherein the growth effective amount of the fertilizer is effective to stimulate growth of the whole cultivated mycorrhizal plant;
- wherein the naturally occurring L-amino acid is present in the fertilizer in an amount effective to stimulate mycorrhiza development and to increase root mass fraction of the fertilized cultivated mycorrhizal plant, which amount is 30% to 80%;
- whereby the growth of the whole cultivated mycorrhizal plant is stimulated and the root mass fraction of the cultivated mycorrhizal plant is increased.

12. The method of claim 11, wherein 30% to 70% by weight of the nitrogen source is the naturally occurring L-amino acid.

13. The method of claim 11, wherein 40% to 80% by weight of the nitrogen source is the naturally occurring L-amino acid.

14. The method of claim 11, wherein the inorganic compound containing nitrogen is nitrate or ammonium.

15. The method of claim 12, wherein the inorganic compound containing nitrogen is nitrate or ammonium.

16. The method of claim 13, wherein the inorganic compound containing nitrogen is nitrate or ammonium.

17. The method of claim 11, wherein the root mass fraction is increased by at least 25%.

18. The method of claim 17, wherein the number of roots, root tips, and the number of fine roots is increased.

19. The method of claim 11, wherein the preservative is selected from the group consisting of benzoates, acetic acid, salicylic acid, propionic acid, sorbic acid, citric acid, and alexin plus.

* * * * *